(12) United States Patent
Sun et al.

(10) Patent No.: US 6,592,671 B2
(45) Date of Patent: Jul. 15, 2003

(54) APPARATUS FOR CLAMPING A PLANAR SUBSTRATE

(75) Inventors: Hoi Cheong Steve Sun, Monmouth Junction, NJ (US); Bogdan Brycki, Mt. Laurel, NJ (US)

(73) Assignee: Delsys Pharmaceutical Corporation, Monmouth Junction, NJ (US)

( * ) Notice: Subject to any disclaimer, the term of this patent is extended or adjusted under 35 U.S.C. 154(b) by 0 days.

(21) Appl. No.: 09/769,227

(22) Filed: Jan. 25, 2001

(65) Prior Publication Data

US 2001/0002283 A1 May 31, 2001

Related U.S. Application Data

(63) Continuation of application No. 09/095,321, filed on Jun. 10, 1998, now Pat. No. 6,399,143, which is a continuation-in-part of application No. 08/630,012, filed on Apr. 9, 1996, now Pat. No. 5,788,714.

(51) Int. Cl.[7] .................................................. B05B 5/00
(52) U.S. Cl. ........................ 118/625; 118/624; 118/500
(58) Field of Search ............................... 118/621, 308, 118/500, DIG. 2, 319, 624, 625, 626, 630, 632, 636, 640; 279/3, 128; 204/198, 297.03, 297; 269/21; 427/458, 469, 474, 475, 477, 481

(56) References Cited

U.S. PATENT DOCUMENTS 4,652,318 A * 3/1987 Masuda et al. .......... 156/89.19
5,155,652 A * 10/1992 Logan et al. ................ 279/128
5,532,903 A * 7/1996 Kendall ....................... 361/234
5,743,965 A * 4/1998 Nishimura et al. .......... 118/319
5,788,814 A * 8/1998 Sun et al. ............... 118/DIG. 2
6,294,024 B1 * 9/2001 Sun et al. .................... 118/624

FOREIGN PATENT DOCUMENTS

| GB | 2 149 697 | * 6/1985 |
| GB | 2149697 | * 6/1985 |
| JP | 404147643 A | * 5/1992 |

OTHER PUBLICATIONS

IBM Technical Disclosure Bulletin, Combined Contactless Electrostatic and Vacuum Wafer Chuck, Mar. 1985.*

* cited by examiner

Primary Examiner—Richard Crispino
Assistant Examiner—George R. Koch, III
(74) Attorney, Agent, or Firm—Dechert LLP (57) ABSTRACT

The disclosure relates to an apparatus for electrostatically adhering grains to a planar substrate comprising:

a. an electrostatic chuck having a collection surface with at least one grain collection zone for, when the planar substrate is layered on the collection surface, electrostatically directing charged grains to a corresponding surface on the planar substrate; and b. a pattern of holes through the electrostatic chuck allowing a source of low pressure to act through the electrostatic chuck to adhere the planar substrate.

14 Claims, 8 Drawing Sheets

APPARATUS FOR CLAMPING A PLANAR SUBSTRATE

This application is a continuation of U.S. application Ser. No. 09/095,321, filed Jun. 10, 1998, now U.S. Pat. No. 6,399,143 B1.

The present invention relates to a apparatus and method for using a vacuum chuck to assure adhesion of a planar substrate, while using electrodes to attract grains (e.g., dry powder) to adhere to the planar substrate. The electrodes may also participate in holding the planar substrate.

In the field of semiconductor processing, semiconductor wafers have been held in place for processing with clamps, magnetic clamps, electrostatic chucks and vacuum chucks. Such semiconductor processing typically seeks to direct mask material, mask developing materials such as photoresist, dopant and etchant to the semiconductor. In directing etchant to the semiconductor, electromagnetic fields may be used to direct the majority of etching to occur in a given direction; such directed etching processes were not intended to coat the semiconductor with grains. For example, Weeks et al., U.S. Pat. No. 5,692,873, McKinley et al., U.S. Pat. No. 5,724,121 and Hasegawa et al., U.S. Pat. No. 5,676,758 all describe vacuum chucks in connection with various semiconductor apparatuses, and also mention that electrostatic chucks can also be used to clamp the semiconductor wafer. A Di Milia et al. patent, U.S. Pat. No. 4,551,192, describes a pinchuck that can be used to hold a substrate during a lithography process using vacuum or electrostatic forces.

Electrostatic chucks can be used to direct grains of material to a substrate to provide a coated substrate. Various methods can be used to assure that such coating techniques apply an accurate and, in some cases, spatially resolved, coating of material, making it feasible to use electrostatic coating technology to apply pharmaceuticals. Examples of technology in this area include Sun, "Chucks and Methods for Positioning Multiple Objects on a Substrate," U.S. Pat. No. 5788,814, issued Aug. 4, 1998; Sun et al., "Electrostatic Chucks," U.S. Pat. No. 5,858,099, issued Jan. 12, 1999; Pletcher et al., "Method and Apparatus for Electrostatically Depositing a Medicament Powder Upon Predefined Regions of a Substrate," U.S. Pat. No. 6,007,630, issued Dec. 28, 1999; and Sun et al., "Acoustic Dispenser," U.S. Pat. No. 5,753,302, issued May 19, 1998. These documents are incorporated by reference herein in their entirety.

In the course of testing such accurate deposition apparatuses to coat flexible planar substrates, applicant has discovered that while the electrostatic chuck can be used to hold the planar substrate and direct the electrostatic deposition of grains, a combination further using vacuum forces on the chuck increases the processing efficiency such that the planar substrate more reproducibly becomes adhered without deformations and air pockets. Such a combination preferably takes the form of a vacuum chuck onto which is layered a thin, e.g., about 25 $\mu$m to about 250 $\mu$m thick electrostatic chuck having holes through which the vacuum is communicated to the planar substrate.

SUMMARY OF THE INVENTION

In one embodiment, the invention relates to an apparatus for electrostatically adhering grains to a planar substrate comprising:
a. an electrostatic chuck having a collection surface with at least one grain collection zone for, when the planar substrate is layered on the collection surface, electrostatically directing charged grains to a corresponding surface on the planar substrate; and
b. a pattern of holes through the electrostatic chuck allowing a source of low pressure to act through the electrostatic chuck to adhere the planar substrate.

The apparatus can further comprise:
c. a low pressure chuck having an adhesion surface having a plurality of holes for aligning with the holes to connect the holes to the source of low pressure.

The adhesion surface can be a porous material.

In one embodiment, the electrostatic chuck comprises (i) the collection surface, (ii) a dielectric layer located behind the collection surface, (iii), behind the dielectric layer, one or more attraction electrodes for attracting grains to the collection zones. Also, the electrostatic chuck can further comprises (iv) one or more shield electrodes for discouraging charged grains from being directed away from the collection zones. A rotatable cluster of a plurality of said low pressure chucks can be used, where the low pressure chucks rotate to repeatedly and sequentially present the adhesion surfaces to the charged grain dispenser. A low pressure control mechanism can be operated to sequentially apply low pressure to low pressure chucks and sequentially releasing the low pressure from low pressure chucks such that there is a contiguous collection of the low pressure chucks to which low pressure is applied and a contiguous collection of the low pressure chucks with no applied low pressure, thereby allowing a sheet of planar substrate to be presented to the charged grain dispenser while adhered to an electrostatic chuck and low pressure chuck and then released for further processing.

Also provided is an electrostatic deposition apparatus for electrostatically depositing grains onto a planar substrate comprising:
i. at least one low pressure chuck having an adhesion surface having a plurality of holes for conveying low pressure to the adhesion surface;
ii. layered on the collection surface, at least one electrostatic chuck having a collection surface with at least one grain collection zone for, when the planar substrate is layered on the collection surface, electrostatically directing charged grains to a corresponding surface on the planar substrate, the at least one electrostatic chuck having a pattern of holes through the electrostatic chuck allowing the low pressure to act through the electrostatic chuck to adhere the planar substrate; and
iii. a charged grain dispenser for directing charged grains towards the grain collection zones.

Still further provided is a method of electrostatically applying a grains to a planar substrate comprising:
a. adhering the planar substrate to an electrostatic chuck with a pressure differential conveyed to the planar substrate via passages through the electrostatic chuck;
b. applying a voltage to the electrostatic chuck to attract charged grains to at least one grain collection zone defined by the electrostatic chuck;
c. directing charged grains towards the charged grain collection zone; and
d. electrostatically adhering charged grains on a portion of the planar substrate corresponding to the grain collection zone.

DEFINITIONS

The following terms shall have, for the purposes of this application, the respective meaning set forth below.

delivery to an animal: A delivery device for delivering defined amounts of reagents to an animal delivers such defined amounts to a tissue of the animal. For example, the device can deliver reagents orally, sublingually, rectally, nasally, vaginally, topically (including the use of a patch or other transdermal delivery device), by pulmonary route (for instance by use of an aerosol or powder cloud), or parenterally (including, for example, intramuscularly, subcutaneously, intraperitoneally, intraarterially, intravenously or intrathecally).

dry deposited: A material is "dry deposited" if deposited without applying the material in a liquid vehicle.

excipient: Excipients are pharmaceutically acceptable organic or inorganic carrier substances suitable for parenteral, enteral (e.g., oral or inhalation) or topical application. Preferably, these excipient do not react deleteriously with the active compositions. Suitable pharmaceutically acceptable carriers include but are not limited to water, salt solutions, alcohols, gum arabic, benzyl alcohols, gelatine, carbohydrates such as lactose, amylose or starch, magnesium stearate, talc, silicic acid, hydroxymethylcellulose, polyvinylpyrrolidinone, and the like.

effective amount: The meaning of "effective amount" will be recognized by clinicians but includes amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease, or the symptoms thereof.

electro-attractive dry deposition: This term refers to methods that use an electromagnetic field, or an electrostatically charged surface to dry deposit charged grains (e.g., particles).

grains are, for the purposes of this application, either aggregates of molecules or particles, preferably of at least about 3 nm average diameter, preferably at least about 500 nm or 800 nm average diameter. Grains are, for example, particles of a powder such as a dry powder.

planar substrate is intended to denote a substrate which is predominately formed with two major dimensions, such as a tape or sheet. The term does not imply that the substrate is flat.

DETAILED DESCRIPTION OF THE INVENTION

Combined Electrostatic and Vacuum Clucks

Figure 1A:
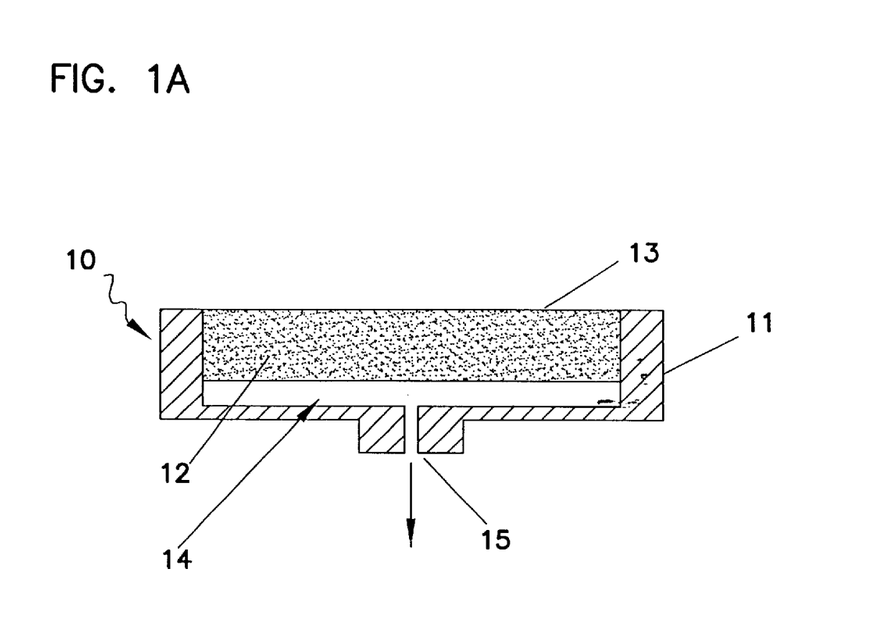
FIG. 1A illustrates a vacuum chuck used with the apparatus for electrostatically adhering grains of the present invention.
Figure 1B:
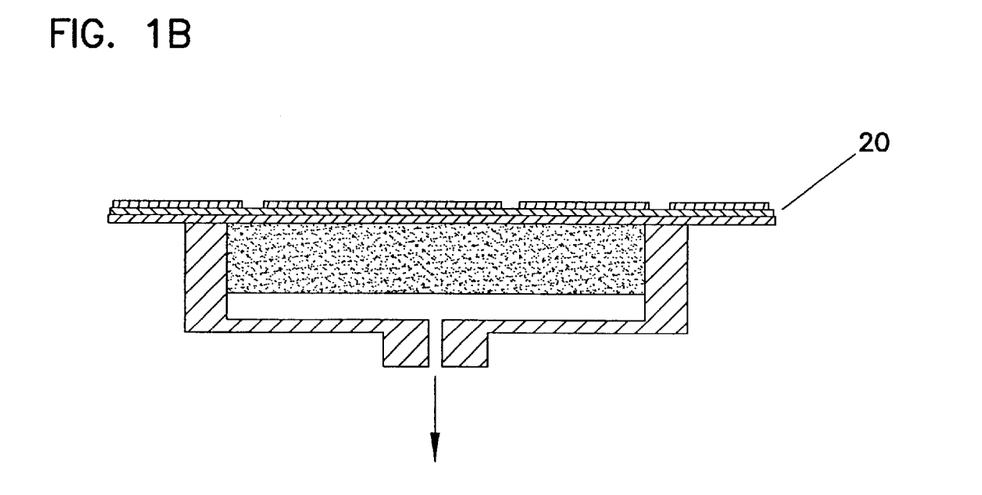
FIG. 1B shows an electrostatic chuck adhered to an adhesion surface of the vacuum chuck.

FIG. 1A illustrates a vacuum chuck used with the apparatus for electrostatically adhering grains of the present invention. The vacuum chuck 10 is made up of a porous disk 11, on which is mounted a porous material 12, such as a sintered material such as a sintered ceramic. The upper surface of the porous material is an adhesion surface 13. Beneath the adhesion surface 13 is a vacuum chuck manifold 14, which connects to a source of low pressure via outlet 15. FIG. 1B shows an electrostatic chuck 20 made up of tree layers (described further below) adhered to the adhesion surface. It should be noted that all references to relative orientation such as "upper," "beneath" and the like are made to facilitate describing the invention with reference to the exempliary drawings, and are not intended to limit the invention.

The illustrated vacuum chuck 10 has a porous disk 11, which can be for example a porous metal such as aluminum or steel, a sintered ceramic, or a sintered glass. The average pores of the disk can be, for example, from out 20 $\mu$m to about 500 $\mu$m, such as about 20 $\mu$m. The vacuum transmitting surface can also be, for example, a surface in which a series of holes have been formed.

Figure 2A:
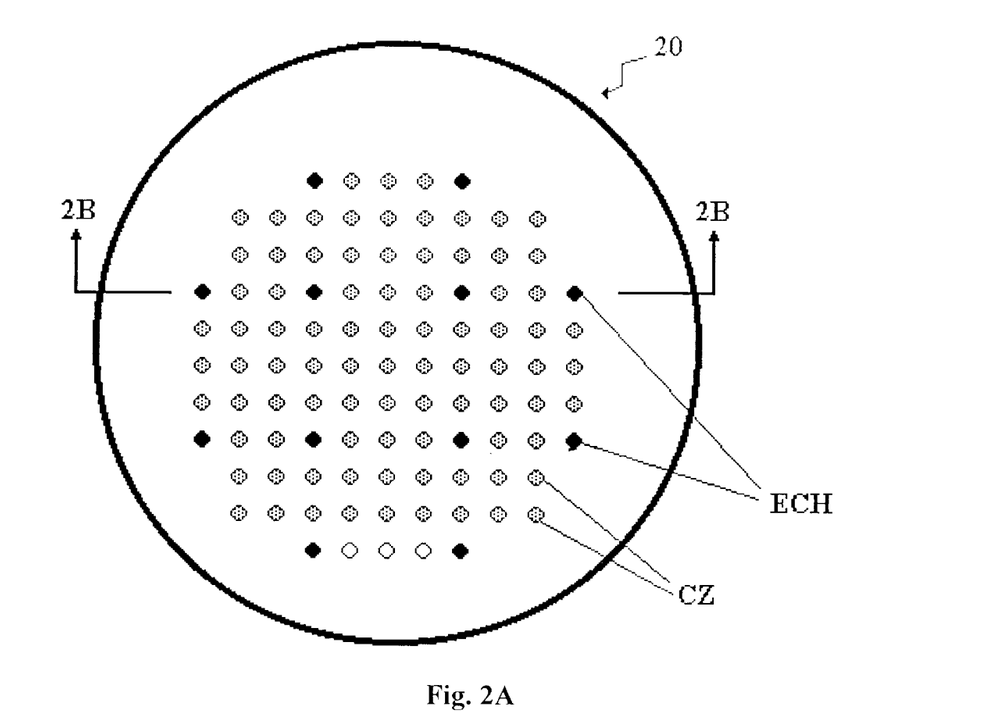
FIG. 2A shows the upper surface of a three-layer electrostatic chuck.
Figure 2B:
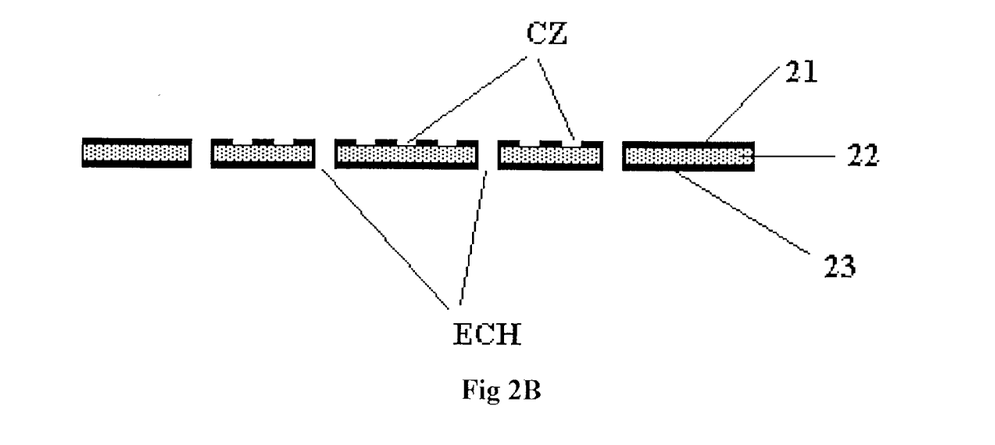
FIG. 2B shows the cross-section indicated in FIG. 2A.

FIG. 2A shows the upper surface of a three-layer electrostatic chuck 20. FIG. 2B shows the cross-section indicated in FIG. 2A. The electrostatic chuck has through holes ECH that allow the vacuum from a vacuum chuck such as vacuum chuck 10 to be conveyed through the electrostatic chuck 20 to the planar substrate. While in many embodiments the electrostatic chuck is adhered to the vacuum chuck by, for example, a clamp or adhesive, the vacuum can assure that the electrostatic chuck, which can be quite thin and flexible, is conformed to an appropriate shape. The electrostatic chuck 20 is made up of a shield electrode 21, a dielectric layer 22 and a grain-attracting electrode 23. Openings in the shield electrode 21 define collection zones CZ. Openings through the electrostatic chuck define the through holes ECH. The grains attracted are typically appropriately charged as described below and in the documents described therein. An appropriate potential, such as without limitation about 200 V to about 2,500 V or to about 3,000 V of a given polarity is applied to the grain-attracting electrode 23, while a ground potential or an opposite potential is applied to the shield electrode 21. (As indicated in copending U.S. Pat. No. 6,149,774, issued Nov. 21, 2000, "AC Waveforms Biasing for Bead Manipulating Chucks," the grain-attracting voltage can be applied in a pulsatile manner, allowing better results in attracting grains to conductive substrates.)

The illustration is not to scale. Electrostatic chucks that have been used with the invention have been, for example, about 10 cm in diameter, or about 10 by 15 cm. The thickness of the shield electrode is, for example, about 0.1 $\mu$m to about 50 $\mu$m, or about 10 $\mu$m to about 25 $\mu$m. The thickness of the dielectric layer is, for example, about 10 $\mu$m to about 75 $\mu$m, or about 15 $\mu$m to about 25 $\mu$m. The thickness of the grain-attracting electrode is, for example, about 0.1 $\mu$m to about 50 $\mu$m, or about 15 $\mu$m to about 25 $\mu$m. These thicknesses are selected to assure that the bead-attracting electrode can create a sufficient field to attract grains to regions of the planar substrate located above the collection zones CZ. Additionally, the thickness of the dielectric layer 22 and the planar substrate can be selected so that, once deposited on the planar substrate, the charged grains cause charge redistributions in the grain-attracting electrode that create an image force that can be larger than that due to the voltage applied to the grain-attracting electrode.

In one embodiment, the grain-attracting electrode 23 can be fabricated by depositing, using known techniques, such as using a 5000 Angstrom layer of gold (Au) onto the dielectric layer 22. Alternatively, grain-attracting electrode 23 can comprise, for example, a 100 Angstrom layer of chromium (Cr) and with a 5000 Angstrom gold (Au) overcoat. Dielectric layer 22 can be made of, for example, Dupont® Kapton® polyimide film (type 300 HN, for example, 3 mil thickness, from Dupont DeNemours, Willmington, Del.) or on Corning Pyrex 7740 glass, for example of 10 mils thickness (Corning Glass, Corning, N.Y.). Shield electrode 21 can comprise, for example, a 35 micron deposition of copper (Cu) onto the dielectric layer 22.

Figure 3A:
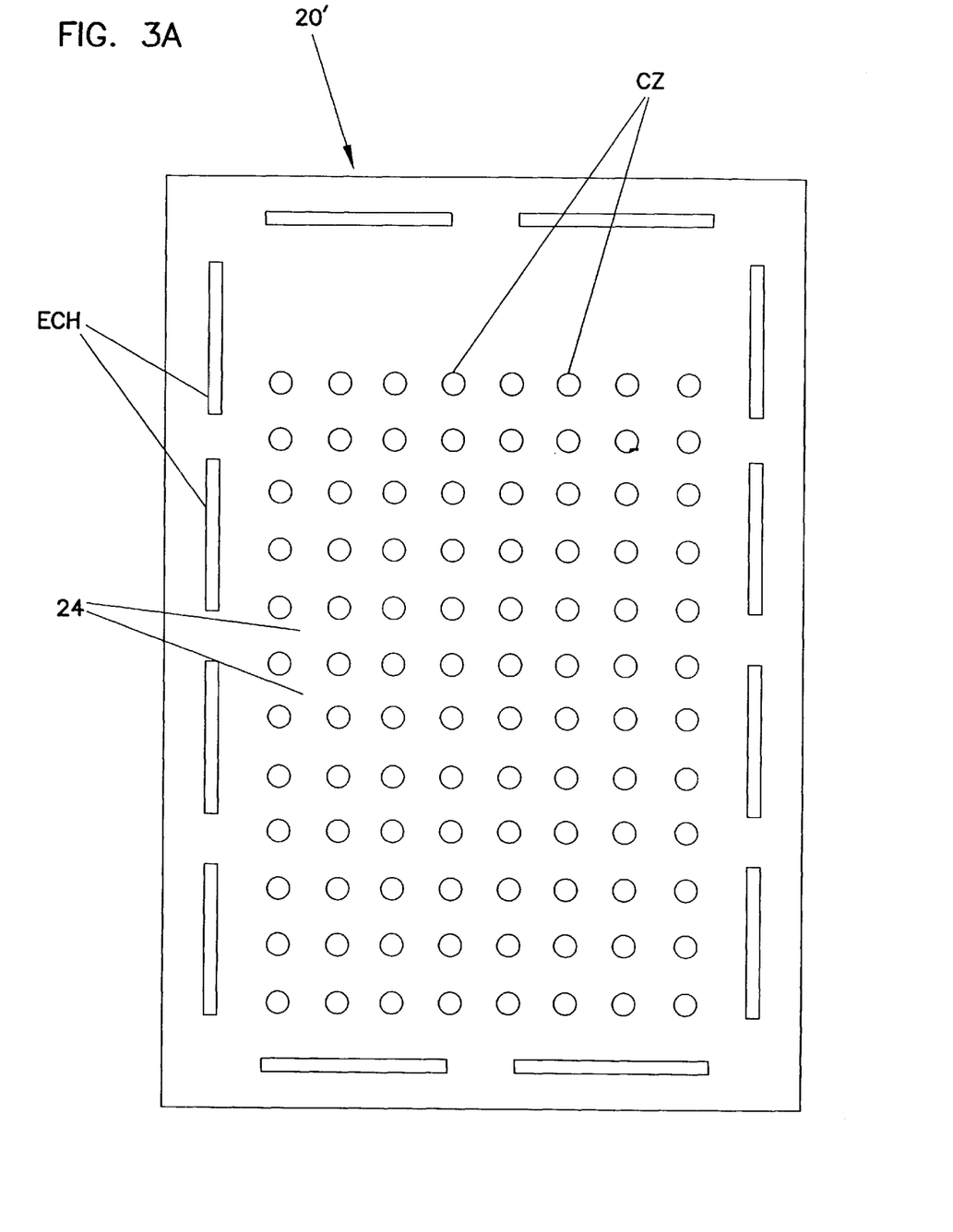
FIG. 3A shows the upper surface of another electrostatic chuck.
Figure 3B:
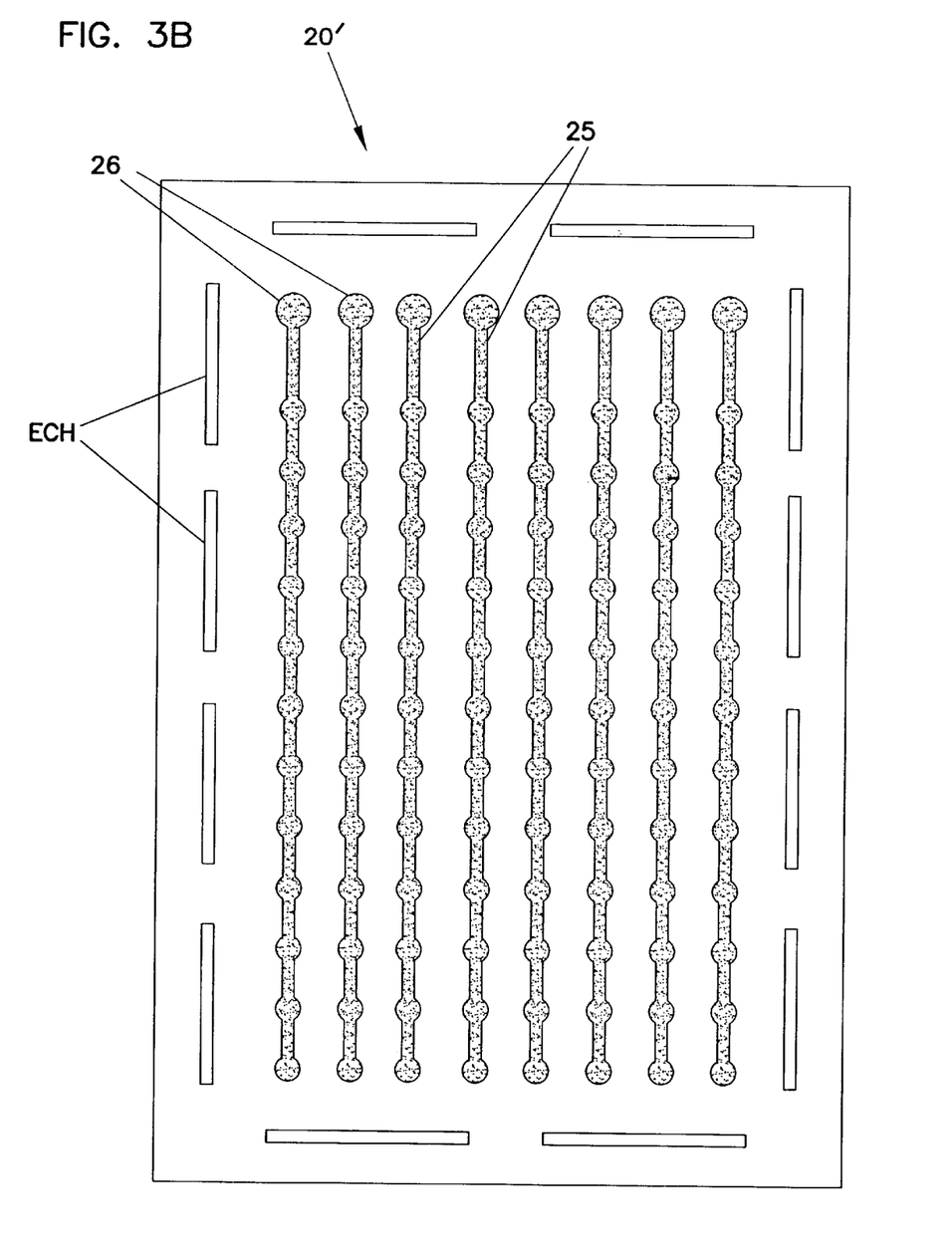
FIG. 3B shows a rear surface of the electrostatic chuck.
Figure 3C:
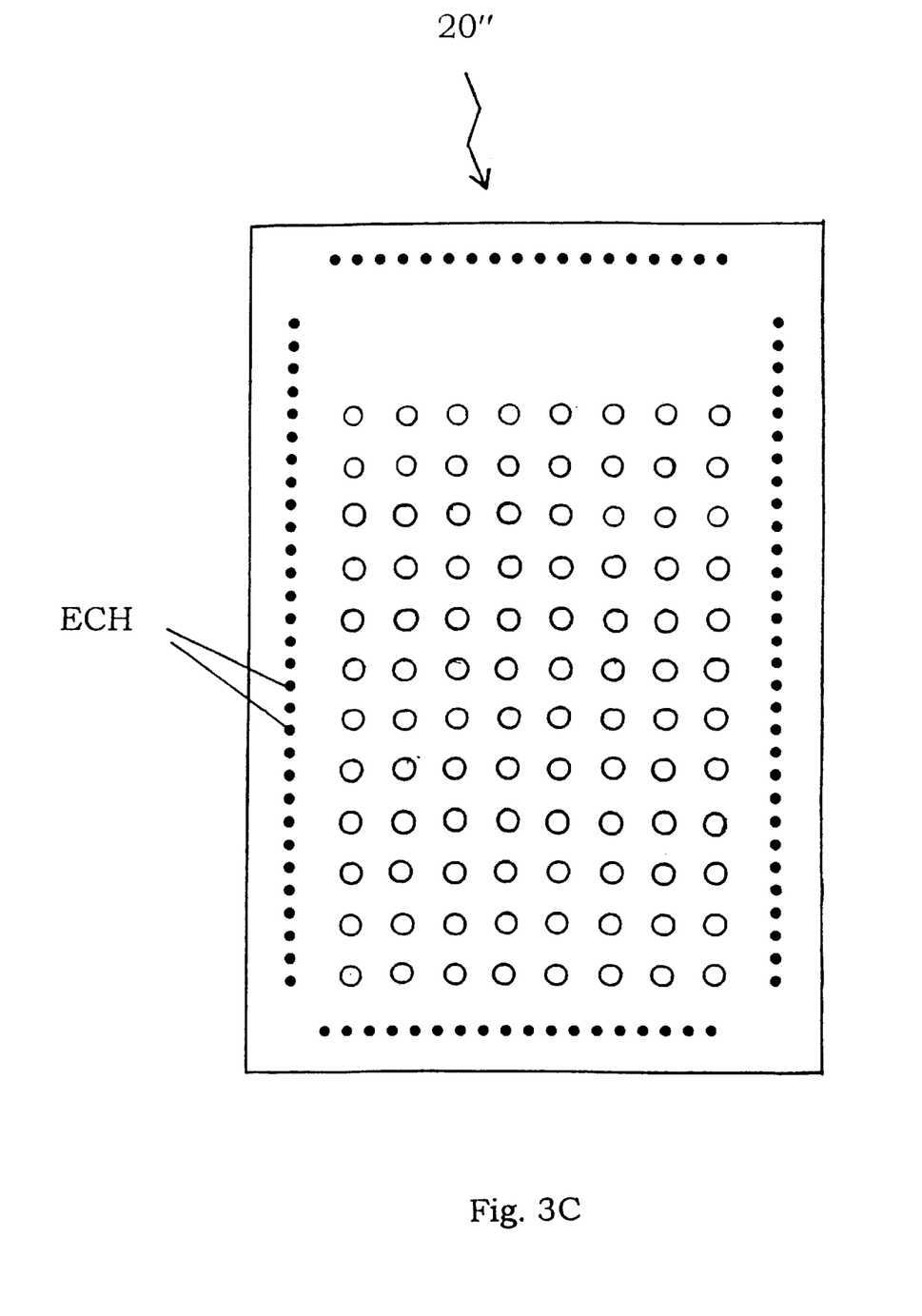
FIG. 3C shows an alternative embodiment where the through holes are rounded holes instead of slots.

FIG. 3A shows the upper surface of electrostatic chuck 20', which differs from electrostatic chuck 20 by having electrostatic chuck through holes ECH that are slots and located on the periphery of the electrostatic chuck 20'. The collection zones CZ are located on a surface 24 otherwise composed of a dielectric material. The through holes ECH are less susceptible to blockage by dust and other particles. FIG. 3B shows a rear surface of the electrostatic chuck 20', which has addressing electrodes 25 through which each row of the electrodes forming the collection zones CZ can be connected to driving electronics. Electrical contact pads 26 provide contact points for connections to voltage sources. FIG. 3C shows an alternative embodiment where the through holes ECH are rounded holes instead of slots.

Figure 4A:
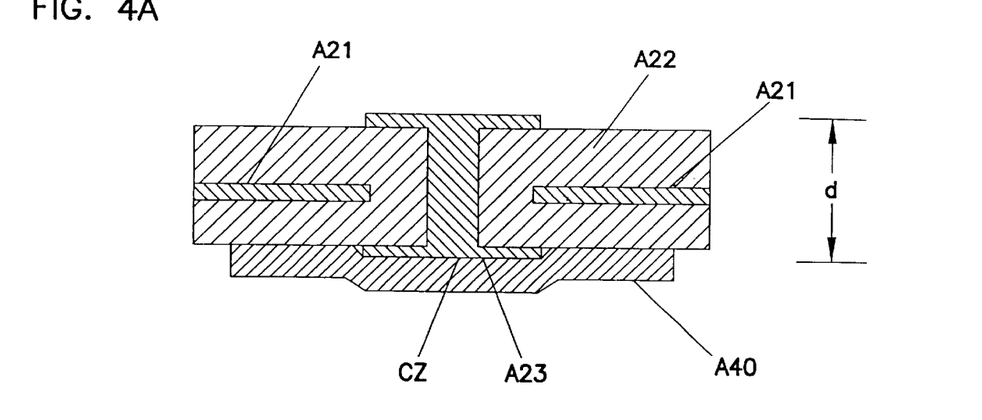
FIGS. 4A–4C show cross-sections of various alternative designs for electrostatic chucks.
Figure 4B:
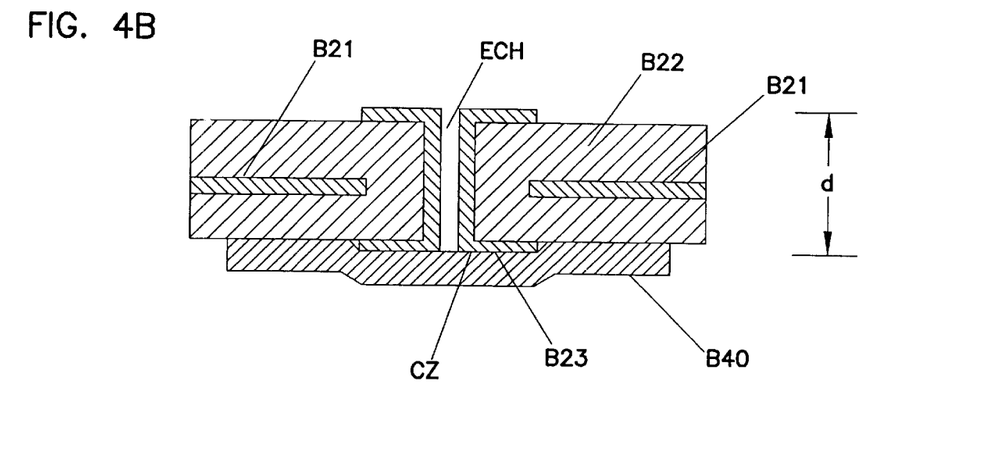
Figure 4C:
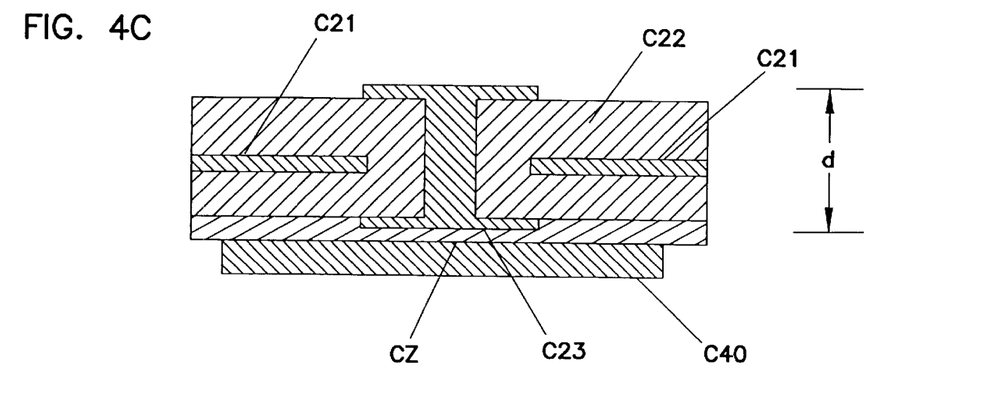

FIGS. 4A–4C illustrate features of electrostatic chucks at a collection zone CZ that can be favorably employed in the invention. In FIG. 4A, the shield electrode A21 (also termed a "ground electrode" based on a preferred bias) is layered within a dielectric A22, which dielectric can be, for example, made of Kaptan® polyimide film (Dupont de Nemours, Wilmington. Del.)(KAPTON® polyimide film can be used as substrate material for Flexible Printed Circuits and can be punched or bonded, etched in alkaline solutions, punched and laser drilled, and can be used to form multilayer polyimide film laminates). The grain-attracting electrode A23 projects out at the surface that attracts the planar substrate A40 (which is, for example, 1 mil thick) and can project out at the opposing side where electrical contacts are formed. The width of the electrostatic chuck d can be, for example, 0.01 inches. As such, the electrostatic chuck can be relatively flexible. In the illustration, the planar substrate wraps over the outwardly projecting grain-attracting electrode A23 in a relatively close-fitting manner. The grain-attracting electrodes typically play a role in adhering the planar substrate. A vacuum chuck used in conjunction with the electrostatic chuck can also contribute to attracting the planar substrate. Tight, smooth adherence of the planar substrate to the electrostatic chuck, which is not disrupted by trapped gas, increases the reliability of grain deposition at the collection zones.

FIG. 4B illustrates an embodiment where the through holes ECH are formed at the grain-attracting electrodes A23. FIG. 4C illustrates an embodiment where an additional layer of dielectric C22 separates the grain-attracting electrode C23 from the planar substrate C40. The electrostatic chuck provided by the configuration of FIG. 4C can be termed a "Pad Indent Chuck" which is useful, for example for depositions of less than about 2 mg, preferably less than about 100 μg, per collection zone CZ (assuming, for example, a collection zone of 3–6 mm diameter, such as 4 mm diameter). The electrostatic chuck provided by the configuration of FIG. 4A can be termed a "Pad Forward Chuck" which is useful, for example for depositions of more than about 20 μg per collection zones CZ (assuming again, a collection zone of 3–6 mm diameter, such as 4 mm diameter), but which is more useful for higher dose depositions than the Pad Indent Chuck.

Planzar Substrate Transporter

Figure 5:
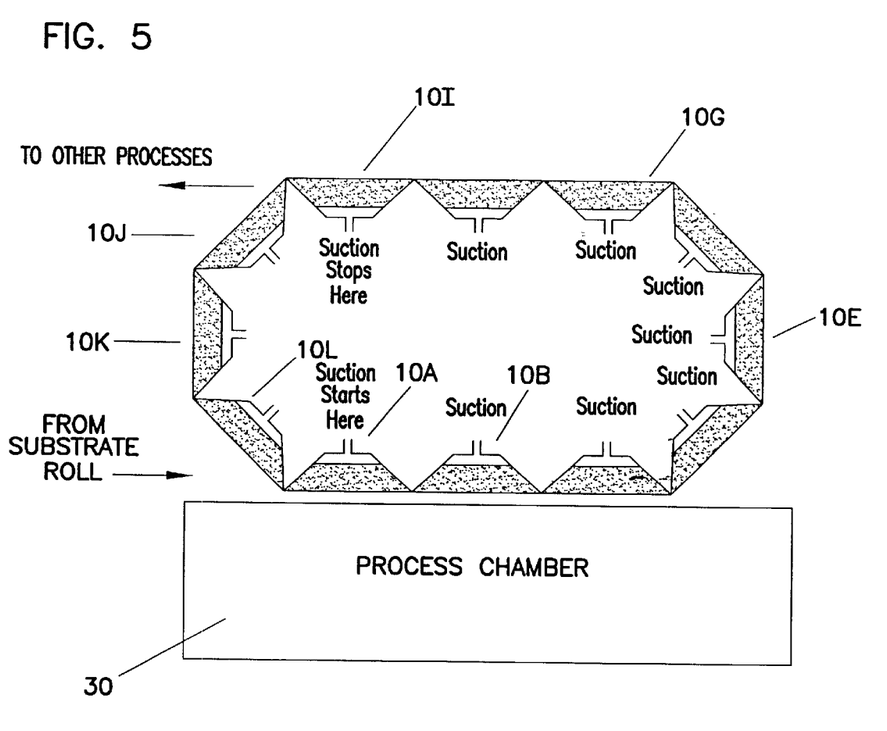
FIG. 5 shows a planar substrate transporter made up of a series of vacuum chucks that define a belt shape.

FIG. 5 shows a planar substrate transporter made up of a series of vacuum chucks 10 that define a belt shape. The rotation of the vacuum chucks 10 around the belt shape can be used to transport a planar substrate through a process chamber 30 at which charged grains are directed at the planar substrate for adhesion mediated by electrostatic chucks positioned on the vacuum chucks 10. The illustrated vacuum chucks 10 rotate around the belt shape, and low pressure is applied to the vacuum chucks as illustrated, allowing suction to be smoothly introduced to a tape (not illustrated) of the planar substrate prior to application of the grains. After application of the grains, the transporter cycles to a point where vacuum is released, allowing the tape of planar substrate to be released and moved to other processes steps. Thus, at time $T_1$, low pressure is applied to vacuum chuck 20A, maintained for vacuum chucks 20B–20H, released for vacuum chuck 20I, and vacuum chucks 20J–20L are maintained at atmospheric pressure. At time $T_2$, which is a time just after that illustrated, low pressure is applied to vacuum chuck 20L, maintained for vacuum chucks 20A–20G, released for vacuum chuck 20H, and vacuum chucks 20I–20K are maintained at atmospheric pressure.

Figure 6:
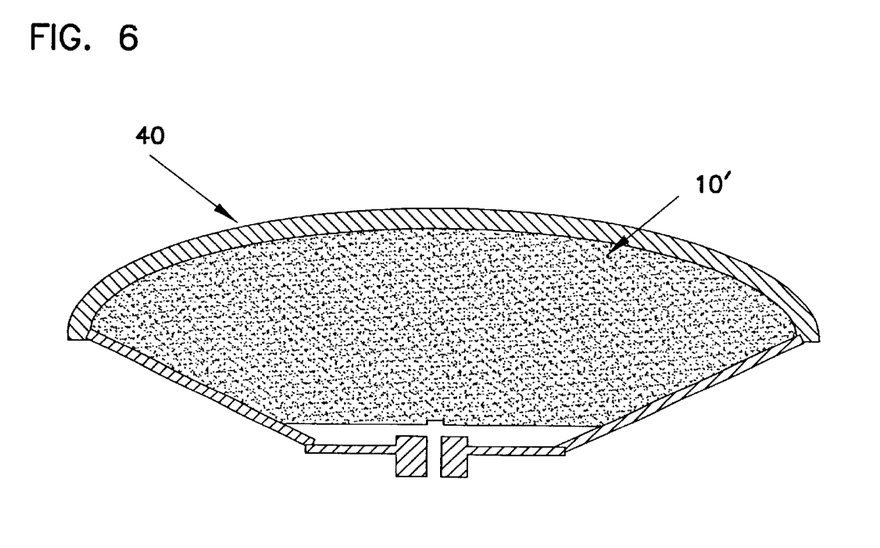
FIG. 6 illustrates a vacuum chuck with a rounded surface.

FIG. 6 illustrates a vacuum chuck 10' with a rounded surface designed to apply a shape to the planar substrate 40 (e.g., spherical, cylindrical, irregular, indented, and the like). Such shaping of the planar substrate 40 can be useful where the coated planar substrate is usefully shaped for later processing, such as in the formation of gelcaps.

Figure 7:
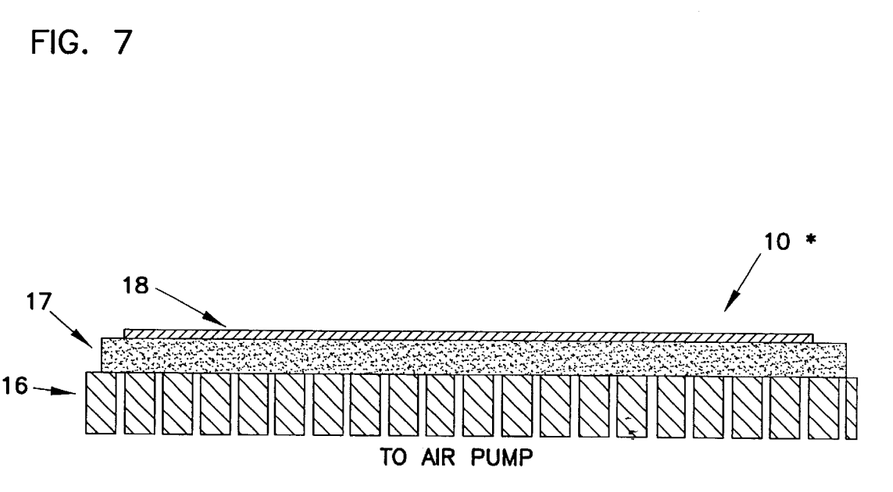
FIG. 7 illustrates a vacuum chuck that utilizes pliable porous materials.

Other, more pliable porous materials can be used in the vacuum chucks used in the invention. A vacuum chuck 10' utilizing such materials is illustrated in FIG. 7, where a rigid or semi-rigid backing plate 16 such as a brass plate with holes or a porous disk as described above is used to support a soft, such as porous Teflon perfluorinated polymer (DuPont de Nemours, Willmington, Del.). The vacuum chuck 10' supports a thin substrate 18.

The planar substrate used with the invention can be any number of materials, but the invention is favorably applied to depositing materials on flexible films such as polyvinylacetate, hydroxypropylmethylcellulose (HPMC), polypropylene, polyester (e.g., Mylar) and polyamide (e.g., nylon) films, which can be plasticized with oils and other known plasticizing agents. One particularly useful embodiment of the invention uses the apparatuses described herein to formulate vehicles for delivering substances to animals, such as vitamins and other bioactive agents, including pharmaceuticals. Accordingly, in many embodiments it is desirable for the planar substrate to be a material suitable for consumption.

Electrostatic and Controlled Field Deposition Methods

In certain electrostatic deposition methods a substrate is sufficiently electrically isolated so that an electrostatic charge can be accumulated on the substrate. One means of accumulating the charge is by taking advantage of the photoelectric effect. In this method the substrate is exposed to ionic bombardment or electromagnetic radiation effective to deposit or strip charges, such as electrons, from the surface of the substrate. Other methods include tribocharging, plasma treatment, induction charging and corona charging. In a more preferred method, an ion emitter is oriented towards the surface on which one intends to create a charge and operated. Such methods of ion printing to controllably electrostatically deposit charged materials such as powders are described in detail in U.S. Pat. Nos. 5,714,007, 6,007,630 and 6,074,688, which documents are incorporated by reference herein in their entirety.

It should be noted that where the average charge-to-mass ratio of the charged particles of the deposition material is known, the mass of particles that will effectively deposit can be relatively accurately predicted from the amount of charge previously accumulated on the substrate. In particular, for a given type of substrate a calibration database can be compiled. For a given average charge-to-mass ratio of the applied particles, the relationship of accumulated charge to deposited mass can be calibrated for a given set of materials and charging conditions. In a production protocol, the average charge-to-mass ratio of the particles can be monitored, for instance using the velocimeter and a modified quartz crystal monitor described in U.S. Pat. Nos. 5,753,302 and 5,858,099, which documents are incorporated herein by reference in their entirety. The illustrative charge-to-mass monitor functions by applying a voltage to a crystal such as a quartz crystal to establish a vibratory frequency, monitoring changes in the vibratory frequency when exposed to the charged particles, and correlating these changes to the mass of the particles that impact the monitor. Another charge-to-mass monitor uses the cage blowoff method of C.B. Schein and J. Cranch, *J. Applied Phys.* 46: 5140, 1975. With the use of one or more charge-to-mass monitors, feedback loops can be incorporated into the electrical controls of a deposition apparatus. In one preferred embodiment, a charge-to-mass monitor is positioned so as to sample the charge-to-mass of particles at their source (examples for source devices described below) and a charge monitor (for example a device for measuring currents created by the deposition of charged particles) is positioned adjacent to the site of deposition. The sampling values produced at these two sites provide diagnostic data on the operation of the deposition apparatus.

A number of additional methods can be used to monitor the amount of material that is deposited on a solid support or substrate. For example, optical methods can include measuring reflectance, transmission, or fluorescence using laser or non-collimated light of broad or narrow band width. Other sources of directed electromagnetic energy can be used, for instance X-ray absorption or fluorescence or microwave absorption can be used. A tuned circuit can be used to monitor an endpoint at which deposited material creates a resonance with an energy source such as a microwave energy source. Acoustic absorption can also be used, where preferably the sound source is an ultrasound source. Another exemplary measuring method can use a profilameter, which is a laser device that measures the amount the a beam of light is deflected by a surface with deposited material to measure the depth of the deposited material. Further electrical methods can include measuring a capacitance between a conductive material associated with the solid support or substrate (for example a conductive material incorporated into the solid support or a conductive material that has the solid support positioned adjacent to it) and another conductor, where the deposited material is located between the two conductors.

A variety of additional factors can be monitored or controlled to increase the reproducibility of the charge-to-mass ratios generated by the charged deposition material source. For example, controlling the humidity of the local environment, the nature and content of bound solvent in the materials sought to be deposited, the purity of materials sought to be deposited, and the rubbing velocity effected in the tribocharging process can be important.

Another method of attracting charged deposition materials to a surface has been termed "controlled field deposition," and typically involves applying a potential to an electrode which directly or indirectly results in the formation of an attractive electrical field at the surface upon which charged material will be deposited. For example, a substrate can have electrical conductors positioned below the deposition surfaces, and a potential applied to the conductors results in the formation of an attractive field at the surface. Where the separation between the substrate's surface and the conductors is sufficiently small, once an external potential is no longer applied to the conductors the charge of the deposition material results in a charge redistribution in the conductors such that an electrostatic "image" force is formed between the deposition material and the conductors, thereby helping to stabilize the deposition material's adherence to the surface.

Figure 8:
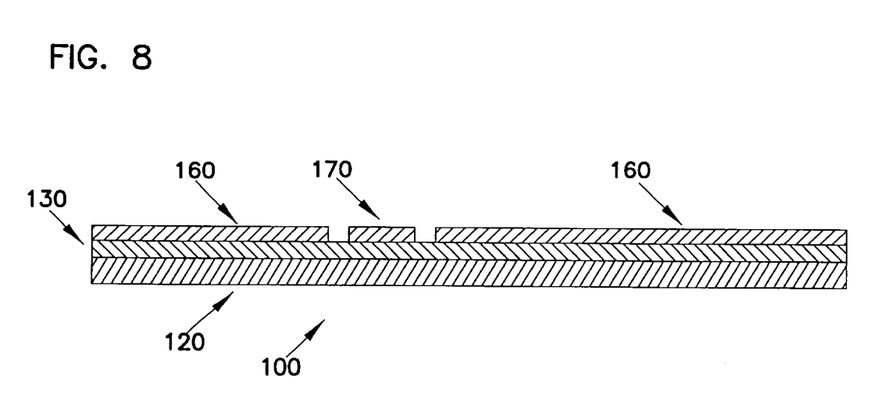
FIG. 8 shows a cross-section of an electrostatic chuck that incorporates a floating electrode.

Further examples of field-generating means include the use of "floating electrodes." A floating electrode is an electrode which develops a localized field as a result of charge redistributions in the floating electrode, which are for example generated by voltages applied across one or more adjacent bias electrodes Thus, for example, as illustrated in FIG. 8, a floating electrode apparatus 100 can have a backing electrode 120, a non-conductive layer 130, a shielding electrode 160 and a floating electrode 170. In the illustrative floating electrode, a bias potential applied across the backing electrode and the shielding electrode (which two electrodes serve as the bias electrodes) causes a charge redistribution in the floating electrode to create the charged-particle attracting field at the floating electrode. Further description of floating electrodes and other forms of field generating devices for controlled field deposition can be found in U.S. Pat. No. 5,858,099, which document is incorporated herein by reference in its entirety. An advantage of floating electrode devices is that the amount of charged particles that will effectively adhere as a result of the field generated at the floating electrode depends on the size of the bias potential. (For more direct field generating apparatuses, the deposition can in principle continue for as long as a potential is applied.)

The field generating devices for controlled field deposition can be designed (a) to directly apply deposition material onto apparatuses that incorporate electrodes for generating the field or (b) for use with electrostatic chucks (i.e., field application structures) which operate in conjunction with the substrate on which deposition material is to be applied. In the former case (a), it is generally desirable that the metallization processes used to create the electrodes is susceptible to mass production techniques. For example, the metallization can be created by lithographic techniques where finely patterned electrodes are sought or by adhering or fusing metal layers to the substrate. In design (b), the electrostatic chuck is generally effective to electrostatically adhere the substrate to the chuck. This adherence of the substrate to the chuck does not depend on the application of any process for creating a charge on the substrate, but instead is believed to be the result of a redistribution of charges in the substrate in response to the field generated by the electrostatic chuck. Of course, a charge on the substrate can usefully be employed to strengthen electrostatic adherence. A third option is that the substrate is designed to reversibly couple with a device that provides the electrodes, such that the substrate and the coupled device provide a field-generating apparatus. In this way, the electrode structures that can be a source of manufacturing costs remain separate from a consumable on which reagents for conducting a chemical process will be deposited. In addition to the documents recited above, further information on electrode structures and electrostatic chucks can be found in U.S. Pat. No. 5,788,814, which document is incorporated herein by reference in its entirety.

The charge of the particles applied to a substrate can be generated for example by plasma treatment, radiation treatment (including treatment with suitably high energy electromagnetic radiation) or ion bombardment. Moreover, the charge can be generated by tribocharging or induction charging (e.g., passing through a tube that is biased to create a field sufficient to induce a charge in grains passing therethrough), wherein two materials with differing triboelectric constants rub against each other and transfer charge between one another. Such methods as tribocharging and induction charging expose the particles to a low amount of reaction-promoting energy, and hence are less susceptible to causing compounds to degrade. Examples of materials that can be used for tribocharging include polytetrafluoroethylene ("TEFLON" polymer), and polymers of chlorotrifluorethylene, chlorinated propylene, vinyl chloride, chlorinated ether, 4-chlorostyrene, 4-chloro-4-methoxy-styrene, epichlorhydrin, styrene, ethylene, carbonate, ethylene vinyl acetate, methyl methacrylate, vinyl acetate, vinyl butyral, 2-vinyl pyridine styrene, and ethylene oxide; as well as polysulfones and nylons. See, for example, "Triboelectrification of Polymers" in K. C. Frisch and A. Patsis, *Electrical Properties of Polymers* (Technomic Publications, Westport, Conn.), which article is hereby incorporated by reference in its entirety. For example, polytetrafluoroethylene and polyethylene and will generally adopt a negative charge and create a positive charge on an object rubbed against them. Nylon and other materials will generally adopt a positive charge and create a negative charge on an object rubbed against them. Tribocharging and appliances for dispensing charged particles are describe in U.S. Pat. Nos. 6,007,630 and 5,753,302. U.S. Pat. No. 5,753,302 describes, in particular, an acoustic dispenser that uses vibratory energy and gating electric fields to dispense charged particles for deposition onto the substrate, and is incorporated herein by reference in its entirety.

In some embodiments, the charged particles may be made up in a wet toner wherein particles of liquid material or liquid material with suspended solids are charged. Charging of the liquid particles can be by, for example, tribocharging occurring at the time the particles are formed, utilizing contact potential differences between solid particles and the particles, or modifying the differences in electrical potential using surface treatments such as surfactants. (See, L. B. Schein, *Electrophotography and Development Physics*, Laplacian Press, 1996, p. 227.) Often it is favorable to dry deposit materials to avoid issues of solubility and stability of a chemical. On the other hand, however, liquid phase depositions are often practical, especially where cautionary procedures, such as limiting the time of exposure to the liquid phase and selecting appropriate carrier solvents, are employed. Liquid phase deposition is for example useful where a material to be deposited is not readily converted to a dry form that can be deposited, or where the non-deposited dry form does not retain an activity such as a biological activity.

Several copending applications or issued patents provide information on dry deposition techniques. For example, methods for use of bead transporter chucks and acoustic grain dispensers are set forth in Pletcher et al., "Apparatus for electrostatically depositing a medicament powder upon predefined regions of a substrate," U.S. Pat. No. 5,714,007, issued Feb. 3, 1998; Pletcher et al., "Method and apparatus for electrostatically depositing a medicament powder upon predefined regions of a substrate," U.S. Pat. No. 6,007,630, issued Dec. 28, 1999; Pletcher et al., "Method and apparatus for electrostatically depositing a medicament powder upon predefined regions of a substrate," U.S. Pat. No. 6,074,688, issued Jun. 13, 2000; Pletcher et al., "Apparatus for electrostatically depositing and retaining materials upon a substrate," U.S. Pat. No. 5,669,973, issued Sep. 23, 1997; Datta et al., "Inhaler apparatus with modified surfaces for enhanced release of dry powders," U.S. Pat. No. 5,871,010, issued Feb. 16, 1999; Sun et al., "Acoustic dispenser," U.S. Pat. No. 5,753,302, issued May 19, 1998; Sun et al., "Electrostatic Chucks," U.S. Pat. No. 5,846,595, issued Dec. 8, 1998; Sun et al., "Method of Making Pharmaceutical Using Electrostatic Chuck," U.S. Pat. No. 5,858,099, issued Jan. 12, 1999; Sun, "Chucks and Methods for Positioning Multiple Objects on a Substrate," U.S. Pat. No. 5,788,814, issued Aug. 4 1998; Loewy et al., "Deposited Reagents for Chemical Processes," U.S. Pat. No. 6,045,753, issued Apr. 4, 2000; Loewy et al., "Solid Support With Attached Molecules," U.S. Pat. No. 6,004,752, issued Dec. 21, 1999; Sun, "Bead Transporter Chucks Using Repulsive Field Guidance," U.S. Pat. No. 6,096,368, issued Aug. 1, 2000; Sun, "Bead manipulating Chucks with Bead Size Selector," U.S. Pat. No 5,988,432, issued Nov. 23, 1999; Sun, "Focused Acoustic Bead Charger/Dispenser for Bead Manipulating Chucks," U.S. application Ser. No. 09/083,487, filed May 22, 1998. Additional instructional information is found in Sun et al., "AC waveforms biasing for bead manipulating chucks," U.S. Pat. No. 6,149,774, issued Nov. 21, 2000; Poliniak et al., "Dry Powder Deposition Apparatus," U.S. Pat. No. 6,063,194, issued May 16, 2000; and "Pharmaceutical Product and Method of Making," U.S. application Ser. No. 09/095,616, filed Jun. 10, 1998.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An apparatus for electrostatically adhering grains to a planar substrate comprising:

a. an electrostatic grain-attracting device having a collection surface with a periphery and a collection area within the periphery comprising at least two grain collection zones for, when the planar substrate is adhered to the collection surface, electrostatically directing charged grains to corresponding surfaces on the planar substrate; and b. a pattern of first holes through the electrostatic grain-attracting device allowing a source of low pressure to act through the electrostatic grain-attracting device to facilitate the adherence of the planar substrate;

wherein the collection surface and holes are configured and patterned to adhere, with the low pressure, a flexible planar substrate and the electrostatic grain-attracting device is adapted to selectively attract grains to the flexible planar substrate at two or more distinct surface areas corresponding to the two or more grain collection zones, and wherein at least one of the following applies:

1. the first holes are at the periphery; or
  2. the apparatus further comprises a vacuum chuck comprising a porous support adapted and configured to support the electrostatic grain-attracting device and convey reduced pressure to the first holes, wherein the porous support comprises pores with an average size of 500 microns or less.

2. The apparatus of claim 1, further comprising a vacuum chuck comprising the porous support adapted and configured to support the electrostatic grain-attracting device and convey reduced pressure to the first holes.

3. The apparatus of claim 1, wherein condition 1 applies.

4. The apparatus of claim 1, wherein condition 2 applies.

5. An apparatus for electrostatically adhering grains to a planar substrate comprising:

a. an electrostatic grain-attracting device having a collection surface with at least two grain collection zones for, when the planar substrate is adhered to the collection surface, electrostatically directing charged grains to corresponding surfaces on the planar substrate, wherein the electrostatic grain-attracting device further comprises one or more shield electrodes positioned for discouraging charged grains from being directed to a location away from the collection zones; and b. a pattern of first holes through the electrostatic grain-attracting device at locations of grain collection zones for allowing a source of low pressure to act through the electrostatic grain-attracting device to facilitate the adherence of the planar substrate;

wherein, with the low pressure, the collection surface is configured to and the holes are patterned to adhere the flexible planar substrate and the electrostatic grain-attracting device is adapted to selectively attract grains to the flexible planar substrate at two or more distinct surface areas corresponding to the two or more grain collection zones.

6. An electrostatic deposition apparatus for electrostatically depositing grains onto a planar substrate comprising:

i. rotatable cluster of a plurality of low pressure chucks, wherein the low pressure chucks rotate to repeatedly and sequentially present the adhesion surfaces to the charged grain dispenser, the low pressure chucks having an adhesion surface, the low pressure chucks comprising first means for conveying low pressure to the adhesion surface;

ii. electrostatic grain-attracting devices adhered to the adhesion surfaces, the electrostatic grain-attracting devices each having a collection surface with at least one grain collection zone wherein, when the planar substrate is adhered to the collection surface, the electrostatic grain-attracting devices effective to electrostatically direct charged grains to a corresponding surface on the planar substrate, the electrostatic grain-attracting devices comprising second means for conveying suction from the low pressure chuck to facilitate adherence of the planar substrate to the collection surface; and iii. a charged grain dispenser for directing charged grains towards the at least one collection zone.

7. The electrostatic deposition apparatus of claim 6, wherein the first means for conveying low pressure to the adhesion surface comprises a plurality of first holes and the second means for conveying low pressure comprising a pattern of second holes through the electrostatic chuck.

8. The electrostatic deposition apparatus of claim 6, further comprising:

iv. a low pressure control mechanism for sequentially applying low pressure to the low pressure chucks and sequentially releasing the low pressure from the low pressure chucks such that there is a contiguous collection of the low pressure chucks to which low pressure is applied and a contiguous collection of the low pressure chucks with no applied low pressure, thereby allowing a sheet of planar substrate to be presented to the charged grain dispenser while adhered to an electrostatic grain-attracting device and low pressure chuck and then released for further processing.

9. An apparatus for electrostatically adhering grains to a planar substrate comprising:

a. a flexible electrostatic grain-attracting device comprising a grain attracting electrode and a collection surface with at least one grain collection zone, wherein, when the planar substrate is adhered to the collection surface, the electrostatic grain-attracting device is effective to electrostatically direct charged grains to surfaces on the planar substrate corresponding to the grain collection zones;

b. a first means for conveying suction through the electrostatic grain-attracting device, allowing a source of low pressure to act through the electrostatic grain-attracting device to facilitate adherence of the planar substrate to the collection surface; and c. a low pressure chuck comprising an adhesion surface having a second means for conveying suction that aligns with the first means to connect the first means to a source of low pressure via the second means for conveying suction, wherein the electrostatic grain-attracting device is adhered to the adhesion surface, and the apparatus provides that force generated by the low pressure acts to conform the electrostatic grain-attracting device to the shape of the adhesion surface.

10. The apparatus of claim 9, wherein the electrostatic grain-attracting device comprises metallic electrodes and a flexible dielectric, the electrostatic grain-attracting device being no more than about 10 mils in thickness.

11. The apparatus of claim 10, wherein the electrostatic grain-attracting device is no more than about 175 microns in thickness.

12. The apparatus of claim 10, wherein the electrostatic grain-attracting device is no more than about 75 microns in thickness.

13. The apparatus of claim 9, wherein the adhesion surface comprises a porous material comprising holes which comprise the second means for conveying suction.

14. An apparatus for electrostatically adhering grains to a planar substrate comprising:

a. an electrostatic grain-attracting device having a collection surface with at least two grain collection zones for, when the planar substrate is adhered to the collection surface, electrostatically directing charged grains to corresponding surfaces on the planar substrate, the grain collection zones adapted to receive potentials biased to create a grain attracting field to effect said directing, wherein the electrostatic grain-attracting device further comprises one or more shield electrodes positioned and adapted for discouraging charged grains from being directed to a location away from the collection zones on application thereto of potential biased to so discourage charged grains; and b. a pattern of first holes through the electrostatic grain-attracting device at locations of grain collection zones for allowing a source of low pressure to act through the electrostatic grain-attracting device to facilitate the adherence of the planar substrate;

wherein the collection surface is configured to and the holes are patterned to adhere, with the low pressure, a flexible planar substrate and the electrostatic grain-attracting device is adapted to selectively attract grains to the flexible planar substrate at two or more distinct surface areas corresponding to the two or more grain collection zones.

* * * * *